US00PP26938P2

(12) United States Plant Patent
Verwer

(10) Patent No.: US PP26,938 P2
(45) Date of Patent: Jul. 12, 2016

(54) ***DAHLIA* PLANT NAMED 'HDNE33'**

(50) Latin Name: *Dahlia hybrida*
Varietal Denomination: HDNe33

(71) Applicant: Aad W. M. Verwer, Lisse (NL)

(72) Inventor: Aad W. M. Verwer, Lisse (NL)

(73) Assignee: Verwer Dahlias B.V., Lisse (NL)

( * ) Notice: Subject to any disclaimer, the term of this patent is extended or adjusted under 35 U.S.C. 154(b) by 156 days.

(21) Appl. No.: 14/120,741

(22) Filed: Jun. 21, 2014

(51) Int. Cl.
*A01H 5/02* (2006.01)

(52) U.S. Cl.
USPC ..... Plt./321

(58) Field of Classification Search
USPC ..... Plt./321
See application file for complete search history.

*Primary Examiner* — Keith Robinson
(74) *Attorney, Agent, or Firm* — C. A. Whealy

(57) ABSTRACT

A new and distinct cultivar of *Dahlia* plant named 'HDNe33', characterized by its compact, mounding and dense plant habit; serrated dark-colored leaves; freely flowering habit; daisy-type inflorescence form; large inflorescences with salmon orange-colored ray florets that are bright yellow in color towards the base; and good postproduction longevity.

2 Drawing Sheets

Botanical designation: *Dahlia hybrida.*
Cultivar denomination: 'HDNe33'.

BACKGROUND OF THE INVENTION

The present invention relates to a new and distinct cultivar of *Dahlia* plant, botanically known as *Dahlia hybrida*, and hereinafter referred to by the name 'HDNe33'.

The new *Dahlia* plant is a product of a planned breeding program conducted by the Inventor in Lisse, The Netherlands. The objective of the breeding program is to create new compact container *Dahlia* plants with dark-colored leaves, large inflorescences and good postproduction longevity.

The new *Dahlia* plant originated from a cross-pollination conducted by the Inventor in Lisse, The Netherlands in 2008 of an unnamed proprietary seedling selection of *Dahlia hybrida*, not patented, as the female, or seed, parent with *Dahlia hybrida* 'VDTG31', disclosed in U.S. Plant Pat. No. 19,303, as the male, or pollen, parent. The new *Dahlia* plant was discovered and selected by the Inventor as a single flowering plant from within the progeny of the stated cross-pollination in a controlled greenhouse environment in Lisse, The Netherlands during the summer of 2009.

Asexual reproduction of the new *Dahlia* plant by cuttings since the spring of 2010 in a controlled greenhouse environment in Lisse, The Netherlands, has shown that the unique features of this new *Dahlia* plant are stable and reproduced true to type in successive generations.

SUMMARY OF THE INVENTION

Plants of the new *Dahlia* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'HDNe33'.

These characteristics in combination distinguish 'HDNe33' as a new and distinct *Dahlia* plant:

1. Compact, mounding and dense plant habit.
2. Serrated dark-colored leaves.
3. Freely flowering habit.
4. Daisy-type inflorescence form.
5. Large inflorescences with salmon orange-colored ray florets that are bright yellow in color towards the base.
6. Good postproduction longevity.

Plants of the new *Dahlia* differ primarily from plants of the female parent selection in the following characteristics:

1. Plants of the new *Dahlia* are more compact and denser than plants of the female parent selection.
2. Leaves of plants of the new *Dahlia* are darker in color than leaves of plants of the female parent selection.
3. Plants of the new *Dahlia* and the female parent selection differ in ray floret color as plants of the female parent selection have fuchsia red-colored ray florets.

Plants of the new *Dahlia* differ primarily from plants of the male parent, 'VDTG31', in the following characteristics:

1. Plants of the new *Dahlia* are taller than plants of 'VDTG31'.
2. Leaves of plants of the new *Dahlia* are darker in color than leaves of plants of 'VDTG31'.
3. Plants of the new *Dahlia* and 'VDTG31' differ slightly in ray floret color.

Plants of the new *Dahlia* can be compared to plants of the *Dahlia hybrida* 'HDRF155', disclosed in U.S. Plant Pat. No. 23,300. In side-by-side comparisons conducted in Lisse, The Netherlands, plants of the new *Dahlia* differed from plants of 'HDRF155' in the following characteristics:

1. Plants of the new *Dahlia* were more freely branching and denser than plants of 'HDRF155'.
2. Plants of the new *Dahlia* had mostly single leaves whereas plants of 'HDRF155' had mostly compound leaves.
3. Plants of the new *Dahlia* and 'HDRF155' differed in ray and disc floret color.

BRIEF DESCRIPTION OF THE PHOTOGRAPHS

The accompanying photographs illustrate the overall appearance of the new *Dahlia* plant showing the colors as true as it is reasonably possible to obtain in colored reproductions of this type. Colors in the photographs may differ slightly from the color values cited in the detailed botanical description which accurately describe the colors of the new *Dahlia* plant.

The photograph on the first sheet comprises a side perspective view of typical flowering plants of 'HDNe33'.

The photograph on the second sheet is a close-up view of a typical flowering plant of 'HDNe33'.

DETAILED BOTANICAL DESCRIPTION

The photographs and following observations and measurements describe plants grown during the late summer and early autumn in 15-cm containers in an outdoor nursery in Lisse, The Netherlands and under cultural practices typical of commercial container *Dahlia* production. During the production of the plants, day temperatures ranged from 15° C. to 25° C. and night temperatures ranged from 8° C. to 20° C. Plants were pinched one time about three weeks after planting. Plants were three months old when the photographs and description were taken. In the following description, color references are made to The Royal Horticultural Society Colour Chart, 1995 Edition, except where general terms of ordinary dictionary significance are used.

Botanical classification: *Dahlia hybrida* 'HDNe33'.

Parentage:

*Female, or seed, parent*.—Unnamed proprietary seedling selection of *Dahlia hybrida*, not patented.

*Male, or pollen, parent*.—*Dahlia hybrida* 'VDTG31', disclosed in U.S. Plant Pat. No. 19,303.

Propagation:

*Type*.—By vegetative cuttings.

*Time to initiate roots, summer*.—About nine days at soil temperatures about 15° C.

*Time to initiate roots, winter*.—About 13 days at soil temperatures about 15° C.

*Time to produce a rooted young plant, summer*.—About 21 days at soil temperatures about 15° C.

*Time to produce a rooted young plant, winter*.—About 24 days at soil temperatures about 15° C.

*Root description*.—Fine, fleshy.

*Rooting habit*.—Moderately freely branching; dense.

*Tubers*.—Length: About 16 cm. Diameter: About 14 cm. Texture: Corky. Color: Close to 199B.

Plant description:

*Plant and growth habit*.—Compact and mounding plant habit; inverted triangular plant form; freely basal branching with about eight lateral branches developing per plant; dense and bushy appearance; inflorescences held above the foliar plane on strong peduncles; vigorous growth habit.

*Plant height*.—About 30 cm.

*Plant diameter or spread*.—About 33 cm.

*Lateral branches*.—Length: About 25 cm. Diameter: About 1.2 cm. Internode length: About 3 cm to 9 cm. Texture: Smooth, glabrous. Strength: Strong. Color: Close to 146B; distally, close to 187C.

Leaf description:

*Arrangement*.—Opposite, mostly single or compound with three leaflets per leaf.

*Leaf length*.—About 13 cm.

*Leaf width*.—About 6 cm.

*Shape*.—Ovate.

*Apex*.—Acuminate.

*Base*.—Attenuate.

*Margin*.—Serrate; sinuses divergent.

*Venation pattern*.—Pinnate.

*Texture, upper and lower surfaces*.—Smooth, glabrous.

*Color*.—Developing leaves, upper surface: Close to 137A. Developing leaves, lower surface: Close to 146A. Fully expanded leaves, upper surface: Darker than 200A; venation, close to 187B. Fully expanded leaves, lower surface: Close to 147C; venation, close to 187C.

*Petioles*.—Length: About 8 cm to 10 cm. Diameter: About 4 mm. Texture, upper and lower surfaces: Smooth, glabrous. Color, upper and lower surfaces: Close to 152B.

Inflorescence description:

*Appearance and flowering habit*.—Daisy-type inflorescences with ray and disc florets developing acropetally on a receptacle; inflorescences positioned above and beyond the foliar plane on strong peduncles; inflorescences face mostly upright; freely flowering habit with typically about 50 to 60 inflorescences developing per plant.

*Fragrance*.—None detected.

*Time to flower*.—Plants begin flowering about 70 days after planting; flowering continuous during the summer and autumn in The Netherlands.

*Post-production longevity*.—Good postproduction longevity; inflorescences maintain good substance for about twelve days on the plant and for about four days as a cut flower; inflorescences persistent.

*Inflorescence buds*.—Height: About 2 cm. Diameter: About 1.9 cm. Shape: Oblate. Color: Close to 187A; towards the apex, close to 46A.

*Inflorescence diameter*.—About 8.6 cm.

*Inflorescence depth* (*height*).—About 1.8 cm.

*Disc diameter*.—About 2.1 cm.

*Receptacle height*.—About 9 mm.

*Receptacle diameter*.—About 1.3 cm.

*Receptacle color*.—Close to 187B; towards the base, close to 147A.

*Ray florets*.—Number of ray florets per inflorescence: About eight arranged in a single whorl. Length: About 4 cm. Width: About 2.4 cm. Shape: Ovate. Apex: Mucronulate. Base: Attenuate. Margin: Entire. Aspect: Initially upright to roughly perpendicular to the peduncle. Texture, upper and lower surfaces: Smooth, glabrous; velvety. Color: When opening, upper surface: Close to 45A; towards the base, close to 21A. When opening, lower surface: Close to 46A. Fully opened, upper surface: Center, close to 26A; towards the apex and at the base, close to 46A; color does not fade with development. Fully opened, lower surface: Close to 46A; towards the base, close to 50A; color does not fade with development.

*Disc florets*.—Number of disc florets per inflorescence: About 86. Length: About 1.6 cm. Diameter: About 1.5 mm. Shape: Tubular; apex dentate. Color, immature: Apex: Close to 187A. Mid-section: Close to 178B. Base: Close to 160B. Color, mature: Apex: Close to 21B. Mid-section: Close to 178B. Base: Close to 160B.

*Phyllaries*.—Quantity per inflorescence: About five arranged in a single whorl. Length: About 1.5 cm. Width: About 9 mm. Shape: Ovate. Apex: Acute. Base: Attenuate. Margin: Entire. Texture, upper and lower surfaces: Smooth, glabrous. Color, upper and lower surfaces: Close to 200A.

*Peduncles*.—Length, terminal peduncle: About 5 cm. Length, fourth peduncle: About 8 cm. Length, seventh peduncle: About 11 cm. Diameter: About 1 cm. Strength: Strong. Aspect: About 70° to 90° from horizontal. Texture: Smooth, glabrous. Color: Close to 200A.

*Reproductive organs*.—Androecium, present on disc florets only: Quantity per disc floret: Five. Filament length: About 4 mm. Filament color: Close to 3B. Anther shape: Lanceolate. Anther length: About 2 mm. Anther color: Close to 15A. Pollen amount: Moderate. Pollen color: Close to 20B. Gynoecium, present on ray and disc florets: Quantity per floret: One. Pistil length: About 3 mm. Stigma shape: Lanceolate. Stigma color: Close to 12C. Style length: About 2.5 mm. Style color: Close to 150B. Ovary color: Close to 150C. Fruits: Length: About 1.6 cm. Diameter: About 1.5 cm. Texture: Smooth, glabrous. Color: Close to 200A. Seeds: Length: About 5 mm. Diameter: About 8 mm. Color: Close to 187A.

Disease & pest resistance: Plants of the new *Dahlia* have not been shown to be resistant to pathogens and pests common to *Dahlia* plants.

Garden performance: Plants of the new *Dahlia* have exhibited good tolerance to rain and wind and have been observed to tolerate temperatures from about 0° C. to about 40° C.

It is claimed:

1. A new and distinct *Dahlia* plant named 'HDNe33' as illustrated and described.

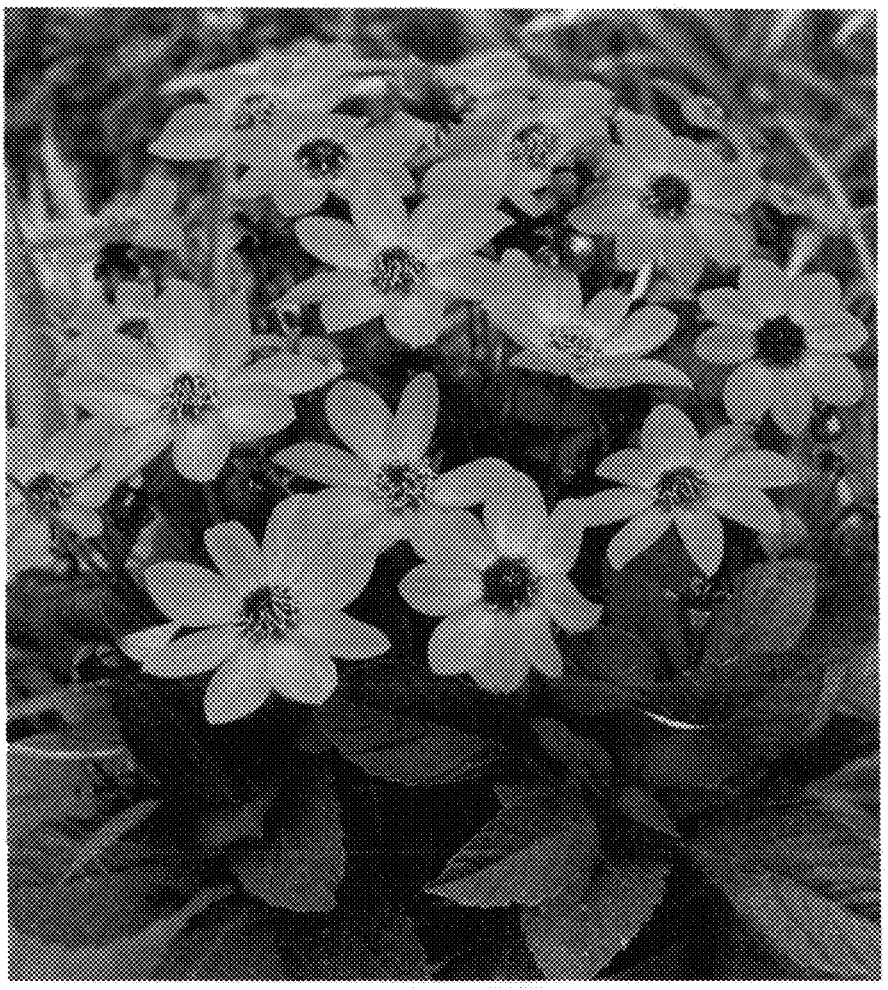

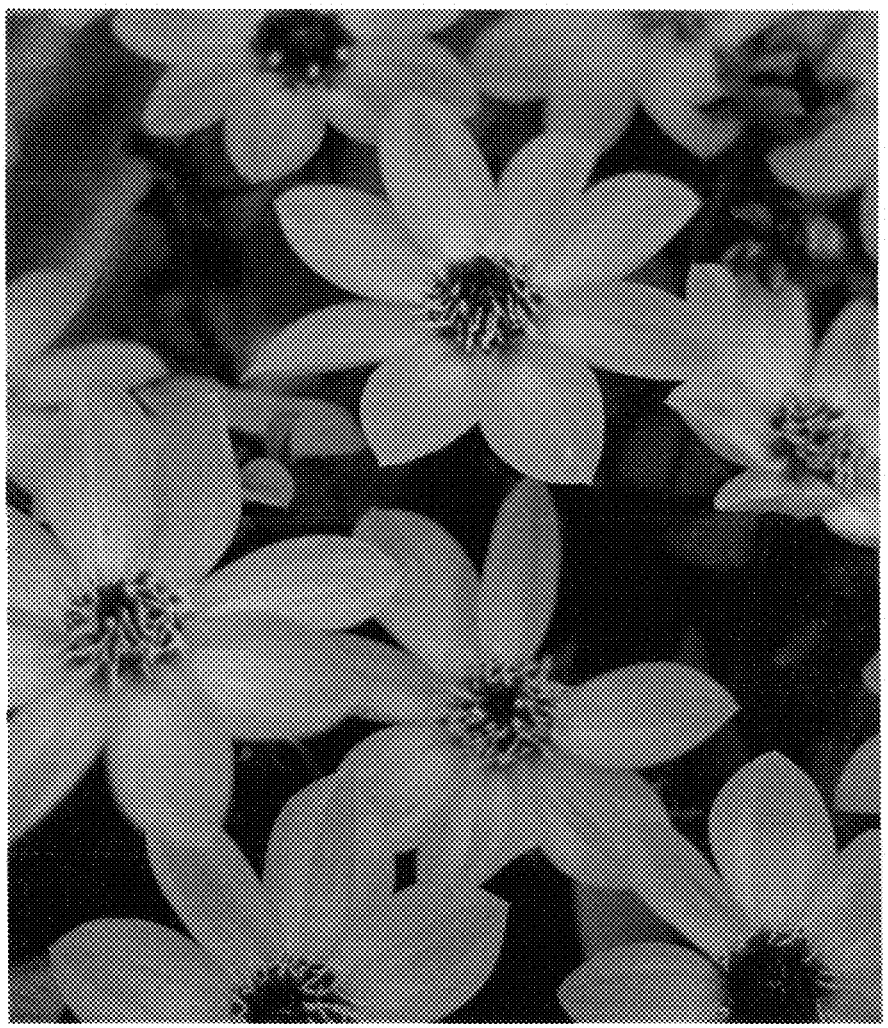

* * * * *